T861004

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED APRIL 1, 1969

861 O.G. 17

622,446

PROCESS FOR PREPARING ACYLALS OF DIALKYLKETENES

James C. Martin and Paul G. Gott, both of P.O. Box 511, Kingsport, Tenn. 37662

Filed Mar. 13, 1967. Published Apr. 1, 1969

Class 260—340.2

No Drawing. 9 Pages Specification

Novel process for preparing acylals of dialkyl ketenes, said acylals being useful and convenient sources of dialkyl ketenes, which comprises reacting a dialkylketene with carbon dioxide in the presence of certain phosphorous catalysts. The catalysts are trivalent phosphorous compounds of the formula $$R^2-\overset{\overset{R^3}{|}}{P}-R^4$$

wherein $R^2$, $R^3$ and $R^4$ are the same or different and each represents an alkyl group of up to about 12 atoms or a phenyl group.